United States Patent
Fonash et al.

(10) Patent No.: US 10,953,370 B2
(45) Date of Patent: Mar. 23, 2021

(54) NANO-PORE ARRAYS FOR BIO-MEDICAL, ENVIRONMENTAL, AND INDUSTRIAL SORTING, FILTERING, MONITORING, OR DISPENSING

(71) Applicant: The Penn State Research Foundation, University Park, PA (US)

(72) Inventors: Stephen J. Fonash, State College, PA (US); Wook Jun Nam, State College, PA (US)

(73) Assignee: The Penn State Research Foundation, University Park, PA (US)

(*) Notice: Subject to any disclaimer, the term of this patent is extended or adjusted under 35 U.S.C. 154(b) by 128 days.

(21) Appl. No.: 15/547,990

(22) PCT Filed: Feb. 5, 2015

(86) PCT No.: PCT/US2015/014596
§ 371 (c)(1),
(2) Date: Aug. 1, 2017

(87) PCT Pub. No.: WO2016/126253
PCT Pub. Date: Aug. 11, 2016

(65) Prior Publication Data
US 2018/0021736 A1    Jan. 25, 2018

(51) Int. Cl.
*B01D 67/00*    (2006.01)
*B01D 69/02*    (2006.01)
(Continued)

(52) U.S. Cl.
CPC ......... *B01D 67/0034* (2013.01); *B01D 69/02* (2013.01); *B01D 69/06* (2013.01);
(Continued)

(58) Field of Classification Search
CPC .............. B01D 67/0034; B01D 69/148; B01D 69/141; B01D 69/06; B01D 69/02;
(Continued)

(56) References Cited

U.S. PATENT DOCUMENTS

| 4,837,049 A | 6/1989 | Byers et al. |
| 6,188,783 B1 | 2/2001 | Balaban et al. |

(Continued)

FOREIGN PATENT DOCUMENTS

| JP | 2004085392 A | 3/2004 |
| WO | 0030534 A1 | 6/2000 |

(Continued)

OTHER PUBLICATIONS

IP.com Search Jun. 26, 2019 (Year: 2019).*

(Continued)

*Primary Examiner* — Pamela H Weiss
(74) *Attorney, Agent, or Firm* — Dinsmore & Shohl LLP

(57) ABSTRACT

Micro- or nano-pores are produced in a membrane for various applications including filtration and sorting functions. Pores with at least one cross-sectional dimension in or near the nano-scale are provided. Device designs and processing allow for the use of thin film disposition and nano-imprinting or nano-molding to produce arrays of nano-pores in membrane materials functioning in applications such as filtration membranes, drug application/control structures, body fluid sampling structures, and sorting membranes. The nano-imprinting or nano-molding approach is utilized to create nano-elements in an organic or inorganic mold material with at least one nano-element cross-sectional dimension in or close to the nano-scale. These nano-elements can be in various shapes including slits, cones, columns, domes, and hemispheres.

9 Claims, 20 Drawing Sheets

(51) Int. Cl.
- *G01N 33/68* (2006.01)
- *G01N 33/543* (2006.01)
- *B01D 69/14* (2006.01)
- *G01N 33/53* (2006.01)
- *G01N 1/28* (2006.01)
- *B82Y 30/00* (2011.01)
- *C12Q 1/68* (2018.01)
- *B01D 69/06* (2006.01)

(52) U.S. Cl.
CPC ......... *B01D 69/141* (2013.01); *B01D 69/148* (2013.01); *C12Q 1/68* (2013.01); *G01N 1/28* (2013.01); *G01N 33/53* (2013.01); *G01N 33/54386* (2013.01); *G01N 33/68* (2013.01); *B01D 2325/021* (2013.01); *B01D 2325/04* (2013.01); *B82Y 30/00* (2013.01)

(58) Field of Classification Search
CPC .......... B01D 2325/04; B01D 2325/021; G01N 33/54386; G01N 33/53; G01N 1/28; G01N 33/68; C12Q 1/68; B82Y 30/00
See application file for complete search history.

(56) References Cited

U.S. PATENT DOCUMENTS

| | | | |
|---|---|---|---|
| 6,515,346 B1 | 2/2003 | Kemeny | |
| 6,936,194 B2 | 8/2005 | Watts | |
| 7,603,153 B2 | 10/2009 | Jacobsen et al. | |
| 8,367,035 B2 | 2/2013 | Rogers et al. | |
| 8,465,655 B1* | 6/2013 | Sun | B82Y 10/00 216/11 |
| 8,666,471 B2 | 3/2014 | Rogers et al. | |
| 9,196,765 B2 | 11/2015 | Yang et al. | |
| 2002/0014621 A1* | 2/2002 | Den | C04B 38/0025 257/3 |
| 2003/0186405 A1* | 10/2003 | Lee | B82Y 30/00 435/182 |
| 2004/0028875 A1* | 2/2004 | Van Rijn | B01D 67/002 428/98 |
| 2004/0065252 A1 | 4/2004 | Sreenivasan et al. | |
| 2004/0065976 A1 | 4/2004 | Sreenivasan et al. | |
| 2005/0191419 A1* | 9/2005 | Helt | B82Y 30/00 427/256 |
| 2006/0054941 A1 | 3/2006 | Lu et al. | |
| 2006/0070868 A1 | 4/2006 | Fan et al. | |
| 2008/0009763 A1 | 1/2008 | Chiou et al. | |
| 2008/0063585 A1 | 3/2008 | Smalley et al. | |
| 2008/0260941 A1* | 10/2008 | Jin | H01F 1/009 427/126.4 |
| 2008/0268288 A1* | 10/2008 | Jin | G03F 7/0002 428/800 |
| 2009/0220561 A1 | 9/2009 | Jin et al. | |
| 2009/0283425 A1 | 11/2009 | Clark et al. | |
| 2010/0209471 A1* | 8/2010 | Weber | A61P 9/10 424/423 |
| 2010/0213963 A1 | 8/2010 | Yoshikawa | |
| 2010/0279179 A1 | 11/2010 | Farrow et al. | |
| 2011/0034860 A1 | 2/2011 | Melsheimer | |
| 2011/0053284 A1* | 3/2011 | Meller | B82Y 15/00 436/149 |
| 2011/0192233 A1* | 8/2011 | Aizenberg | B82Y 10/00 73/861 |
| 2011/0212512 A1* | 9/2011 | Wang | G01N 21/658 435/288.7 |
| 2011/0304317 A1 | 12/2011 | Shalev et al. | |
| 2012/0024775 A1* | 2/2012 | Gong | B01D 69/06 210/500.21 |
| 2012/0037591 A1 | 2/2012 | Tringe et al. | |
| 2012/0041337 A1 | 2/2012 | Ferguson et al. | |
| 2012/0283119 A1 | 11/2012 | Miyahara et al. | |
| 2012/0319705 A1 | 12/2012 | Schober et al. | |
| 2013/0134546 A1 | 5/2013 | Cheng et al. | |
| 2013/0164522 A1 | 6/2013 | Pei et al. | |
| 2013/0165861 A1 | 6/2013 | Ross | |
| 2013/0224394 A1* | 8/2013 | Hanbuecken | B05D 5/12 427/510 |
| 2013/0225956 A1 | 8/2013 | Huang et al. | |
| 2013/0253299 A1 | 9/2013 | Weber et al. | |
| 2013/0256118 A1* | 10/2013 | Meller | B82Y 15/00 204/158.21 |
| 2016/0374585 A1* | 12/2016 | Fonash | A61B 5/053 600/547 |
| 2017/0156652 A1 | 6/2017 | Qiang et al. | |

FOREIGN PATENT DOCUMENTS

| | | | |
|---|---|---|---|
| WO | WO-03084768 A1 * | 10/2003 | .......... A61K 9/0097 |
| WO | 2012064177 A1 | 5/2012 | |
| WO | 2014210306 A1 | 12/2014 | |
| WO | WO-2014210306 A1 * | 12/2014 | .............. A61B 5/04 |

OTHER PUBLICATIONS

James J. Jun, Nicholas A, et al., Fully integrated silicon probes for high-density recording of neural activity. Nature 551, 7679 (2017).

The Economist; Neuroscience; Probing for Answers; A new nerve-cell monitor will help those studying brains; Nov. 11, 2017.

Nabar, Bhargav P. et al., A nanoporous silicon nitride membrane using a two-step lift-off pattern transfer with thermal nanoimprint lithography, Journal of Micromechanics and Microengineering, Mar. 15, 2012, vol. 22, No. 4, Aricle No. 045012 (internal pp. 1-8).

* cited by examiner

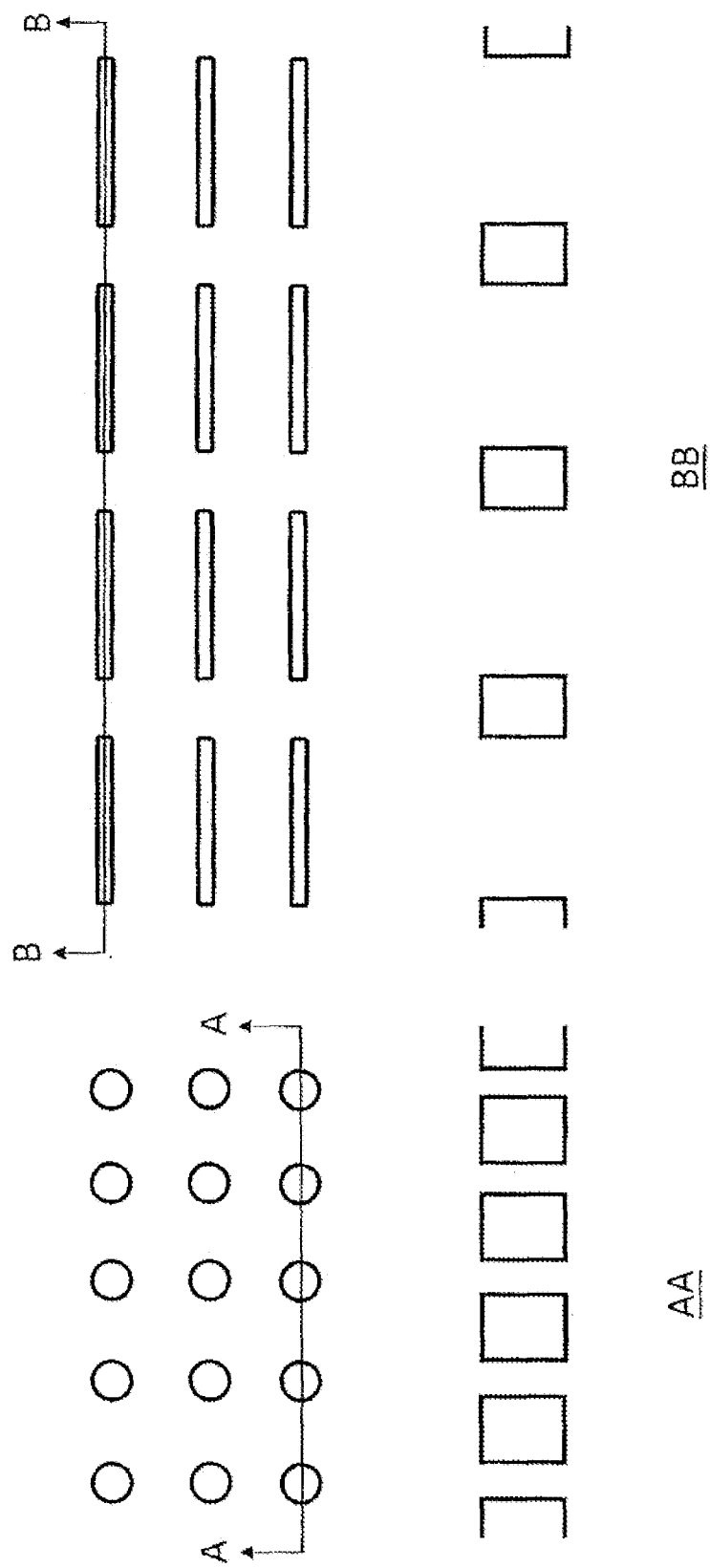

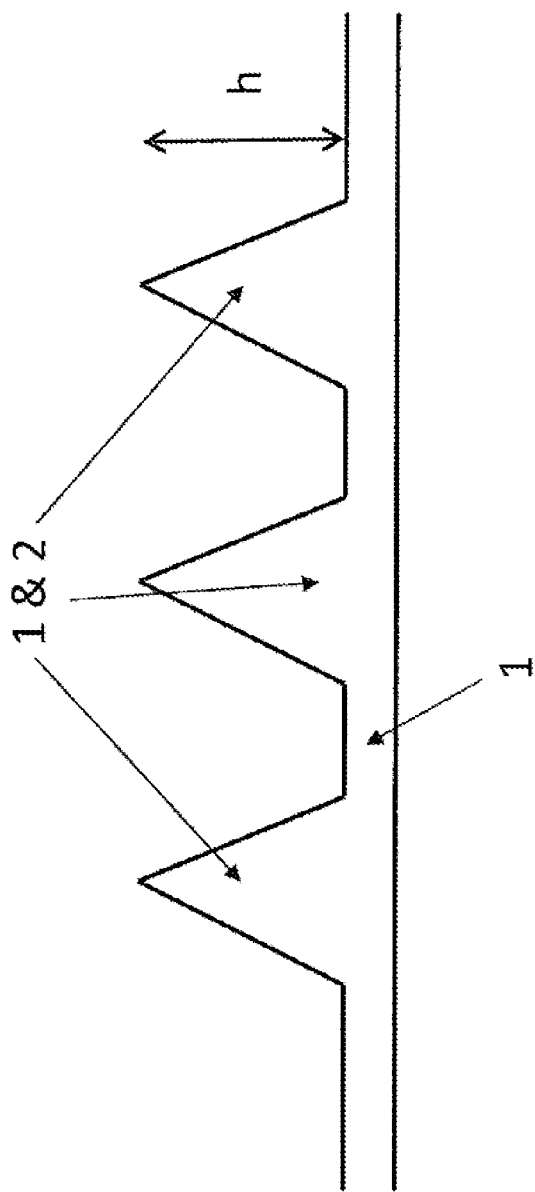

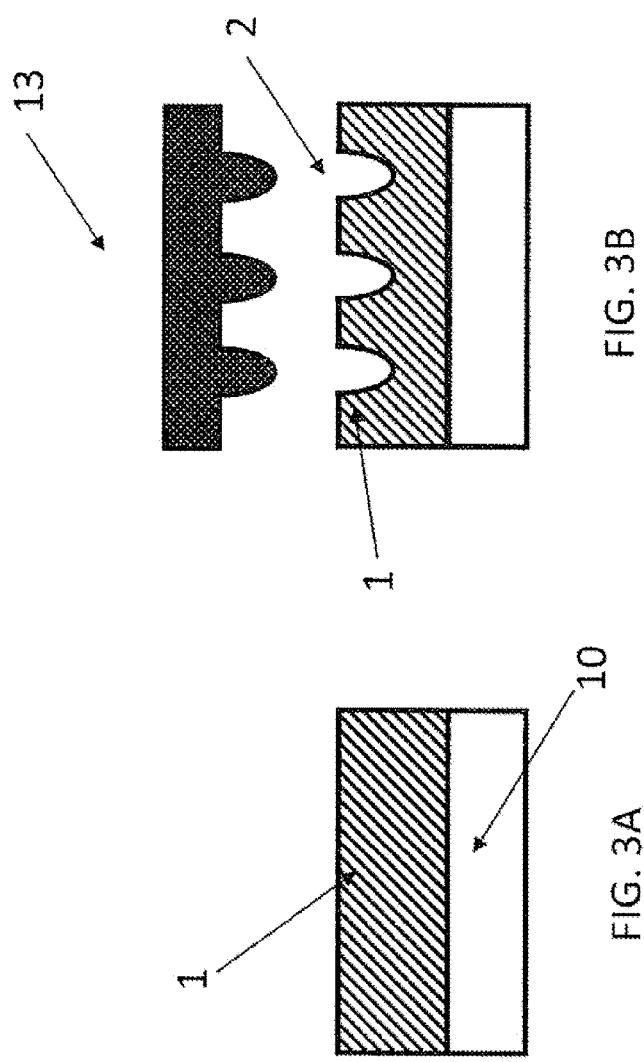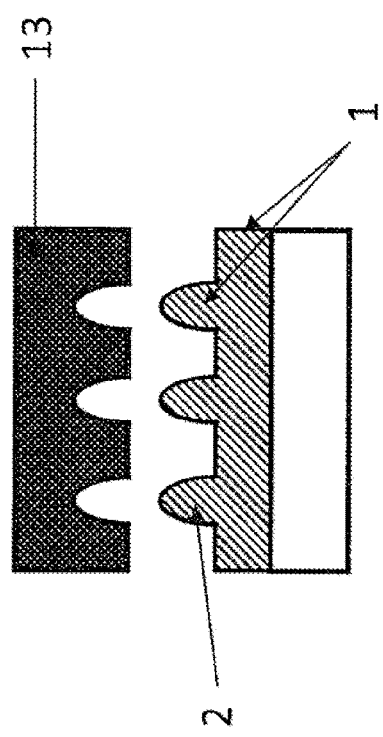
FIG. 3A
FIG. 3B
FIG. 3C

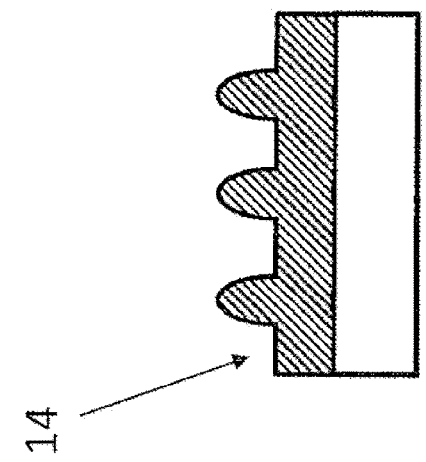
FIG. 4C
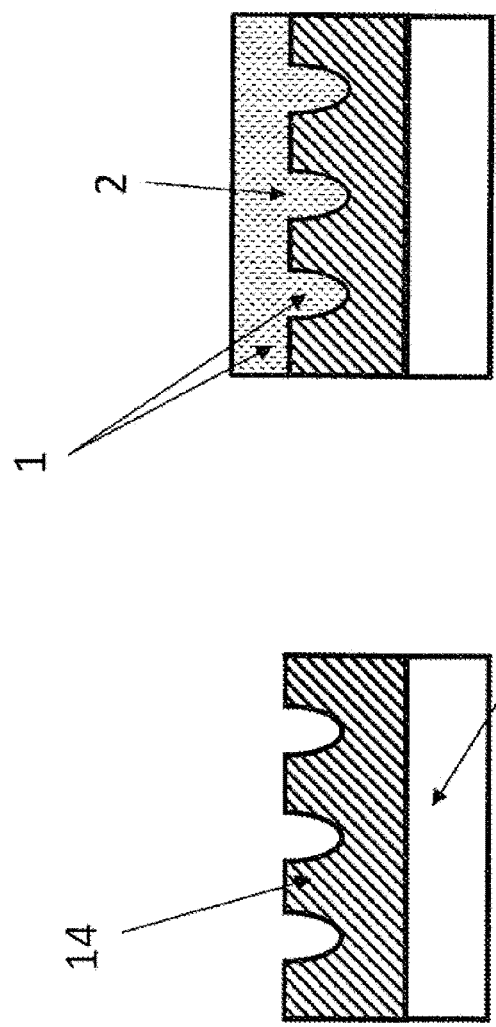
FIG. 4B
FIG. 4A
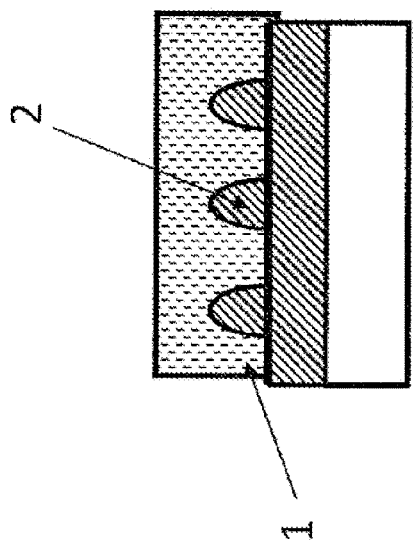
FIG. 4D

NANO-PORE ARRAYS FOR BIO-MEDICAL, ENVIRONMENTAL, AND INDUSTRIAL SORTING, FILTERING, MONITORING, OR DISPENSING

STATEMENT OF GOVERNMENT SUPPORT

This invention was partially made with government support under Grant No. DUE 1205105, awarded by the National Science Foundation. The Government has certain rights in the invention.

CROSS-REFERENCE TO RELATED APPLICATIONS

This application is the U.S. National Phase of PCT/US2015/014596 filed Feb. 5, 2015.

FIELD OF THE INVENTION

The present invention relates to the field of biological and medical (bio-medical) sorting and filtering applications including clinical applications. It also relates to industrial and environmental sorting and filtering applications such as fluid purification processing. In particular, it relates to the design, fabrication, and utilization of nano-pore arrays, serving as sorting and filtering membranes, for various bio-medical, industrial, and environmental applications. The resulting nano-scale or micro-scale nano-pore array structures may function as a filtration membrane or as a drug or chemical dispensing membrane. The pores of these arrays may be arranged to be electrically biased as a whole array or individually biased to further control sorting, filtering, and flow. In addition these nano-pore array membrane structures may use fluid flow to and through the pores and/or electric and/or magnetic fields to trap nano-scale structures at the pore sites. Such trapped, precisely spaced nano-structures arrayed in a membrane may be used for applications, such as drug delivery or sensing or they may be designed to be opto-electronic or electronic devices.

BACKGROUND OF THE INVENTION

Widespread use of prolonged or continuous therapies in medicine has caused a great deal of interest in wearable or implantable devices requiring fluid flow control, monitoring, or both. These devices can be involved in a spectrum of functions from body fluid monitoring and drug dispensing to kidney or lung replacement. A key feature of these functions is the need for membranes containing controlled dimension and sized pores. Conventional polymer filtration membranes currently in use have polydisperse and irregularly shaped pores, making it difficult to achieve the desired hydraulic permeability while maintaining an absolute barrier to macromolecular passage. Typically, the pores in commercially available polymer membranes can be as small as about half a nanometer across. Membranes can be produced in non-polymeric materials by ion track-etching, an approach that can largely eliminate polydispersity in pore size. However, in this case, the membranes tend to be fairly thick and they must have low porosity (<2%) due to the need to minimize the formation of overlapping ion tracks and consequently overlapping pores that would compromise membrane selectivity and immunoisolation (1). As in the case of polymer membranes, track-etched membranes have a random spatial distribution of the pores.

Recently it has been found that these issues with polymer and track-etched membranes can be avoided by utilizing microelectromechanical systems (MEMS) and nanoelectromechanical systems (NEMS) approaches to produce systematic arrays of silicon nanopores for forming filtration membranes (1). Using this MEMS/NEMS approach, which utilizes essentially silicon microelectronics processing, filtration membranes with pores having at least one cross-sectional dimension in the nano-scale, have been fabricated from silicon. MEMS/NEMS silicon nanopore membranes (SNMs) with uniformly sized pores arranged in arrays have been found to be superior to polydisperse porous materials in reducing resistance to fluid flow while maintaining molecular selectivity. Unlike polymeric filtration membranes, controlled pore shape, such as elongated or slit-shaped pores, are possible with these Si MEMS/NEMS filtration membranes. Slit-shaped pores have been shown to provide additional reductions in hydraulic resistance when compared with round or irregular pores (1). Further exploration of Si nanoporous membranes with long, slit-shaped pores has shown their superiority over round pores in terms of hydraulic permeability and molecular selectivity (1-3). Interestingly, the kidney's filters have elongated, slit-shaped structures, rather than the irregular and more cylindrically shaped pores of polymer membranes. Slit pores in 4-µm thick polysilicon membranes have been fabricated as an array of 10 nm×45 µm pores uniformly spaced with 2. mm separation. The argument has been made that Si wafer-based MEMS/NEMS technology should be able to provide $10^{11}$ pores (7 nm×40 µm pores) in a 0.1-m$^2$ membrane, which is a reasonable size for in vivo implantation (1). The pores fabricated by Si MEMS/NEMS have been shown to exhibit smooth surfaces and minimal tortuosity through the thickness of the membrane. Pore size distribution in these membranes showed less than 1% mean variation (1). In general Si wafer-based MEMS/NEMS technology for filtration membranes allows nearly complete control over pore size and shape within sub nanometer fidelity across several centimeters of silicon wafer (1-3).

To limit membrane fouling by globular proteins in silicon nanopore membranes (SNMs) fabricated from silicon by MEMS/NEMS processes, the surfaces of materials in these SNMs have been covalently modified with PEG(1). A number of previous studies have demonstrated that attachment of PEG can significantly reduce protein adsorption and improve biocompatibility of a variety of surfaces. The technique used for PEG attachment in ref 1 involved a single-step attachment to a PEG polymer through a trimethoxysilane group forming a Si—O—Si-PEG sequence by a methanol dehydration reaction. The results of ref 1 and other studies show such surface treatments of silicon can improve Si membrane fouling behavior (1).

Overall membrane characteristics and hydraulic permeability results reported for these Si-based nanopore membranes (SNMs) have led to artificial organ function studies (1-3). In vitro and in vivo testing of SNM membranes shows that their performance matches predicted hydraulic permeability and steric and electrostatic hindrances, and outperforms conventional polymer membranes with round pores. In general, the required pore size and shape for a given application is a function of the ionic strength of the solution, the surface charge of the final membrane material, and fluid-membrane interactions during filtration. Current work indicates that the required pore sizes for bio-medical applications are around 10 nm (1-3). Here and throughout the term pore size refers to the minimum cross-sectional dimension. The term pore is applied to this minimum cross-sectional area region whereas nano-pore refers to the whole structure.

In the case of bio-medical filtration applications, some of the most advanced work in MEMS filtering membranes is currently focused on artificial kidneys (4). The silicon of these artificial kidneys is organized into layers with the Si filtration membrane layers containing millions of MEMS produced slit-shaped pores. The pore size and pore array layout can be exploited to eliminate the need for an internal pump, allowing, instead, the use of natural blood pressure supplied by the heart to run the device (4). In the specific example discussed in Ref 4, alternate spaces between the silicon plates carry fluid and filtrate. The spaces carrying fluid have Si plates whose surfaces are covered with human kidney cells of the type that line the urine-generating tubes (4). These cells, which line the spaces carrying the fluid but not those carrying the filtrate, extract glucose, salts and other desirables from the fluid and transfer them through the pores to the filtrate along with some of the water, just as would happen in a real kidney. What emerges, in different streams, is cleansed blood and urine. The current assessment (4) is that systems like this based on silicon MEMS/NEMS SNMs would be expensive to buy, but cheap to run, and could sustain 95% of patients who die while awaiting a transplant. The cost problem arises for MEMS/NEMS SNMs from the use of standard microelectronics processes. These costs are inexpensive per device when there are billions of devices on a wafer but no so when the whole wafer is essentially the device.

In the case of non-biomedical applications (e.g., environmental and industrial filtration), some of the most advanced work on filtering membranes is focused on water purification (5). For example, desalination plants usually employ a process in which seawater is put under pressure on one side of a polymer membrane. The polymers used are chosen for the pores naturally occurring in a membrane of the materials. These pores are big enough for water molecules to pass, but not big enough for the sodium chloride ions with, as noted earlier, the pores in commercially available polymer membranes being about half a nanometer across.

As is the case for biomedical applications, the avoidance of polymeric materials is also of great interest in non-biomedical applications. Si MEMS/NEMS SNMs are one approach. Graphene based membranes have also been proposed to replace the polymer membranes. In the case of an alternative material such as graphene, the pores of a graphene-based membrane through which the water would pass would have to be fabricated in a manner similar to that employed for Si membranes. Avoiding the use of polymers provides several advantages. First, the pores can be engineered to be of the optimum size. This is found to be 1.2 nm for water desalination, a diameter that permits the passage of water more easily than a polymer membrane does, but is still small enough to exclude hydrated chloride ions, which in turn, hold back the sodium ions since, being negatively charged, the chloride ions attract the positively charged sodium. Second, the pores would all be of the same size, so there would be no gaps large enough to let sodium and chloride ions through. Third, pores fabricated by MEMS/NEMS techniques are straight, rather than being convoluted channels as is the case of the pores in a polymer membrane. This morphology speeds-up the passage of the water molecules. This difference is manifest in lower pressure being needed to desalinate water using systematic nano-pore arrays than is required in a conventional polymer-based system.

In summary current advanced filtration membrane design and fabrication, whether for bio-medical, environmental, or industrial use, is moving away from relying on polymeric materials and is increasingly using silicon-based microelectronics MEMS/NEMS type processing to create nano-pore arrays with controlled size and spatial distribution. Several pore shapes fabricated using Si MEMS/NEMS processing are shown schematically in FIG. 1. Materials that are now being used or proposed for MEMS/NEMS nano-pore membrane formation vary from silicon to graphene. Several pore shapes fabricated using current Si MEMS/NEMS processing are shown schematically in prior art FIG. 1

However, Si-based MEMS/NEMS processing has versatility, materials and fabrication costs limitations. Thus, there exists a need for a new type of manufacturable nano-pore material structure having controlled pore dimensions and array size and applications versatility. There further exists a need for such a material structure having a controlled thickness that can be fashioned from a variety of compositions in response to the application.

SUMMARY OF THE INVENTION

Nano-imprinting or nano-molding processing is used together with thin film disposition to produce micro- or nano-pores assembled in arrays in a membrane for various applications including filtration and sorting functions. While the emphasis in this disclosure is on pores with at least one cross-sectional dimension in or near the nano-scale, it should be appreciated that the invention is not so limited. While the emphasis is on nano-imprinting and nano-molding, their micro-scale counterparts are also covered by the invention herein. The invention incorporates device designs and processing that allow the use of thin film disposition and nano-imprinting or nano-molding to produce arrays of nano-pores in membrane materials functioning in applications such as filtration membranes, drug application/control structures, body fluid sampling structures, and sorting membranes. The nano-imprinting or nano-molding approach is utilized to create nano-elements in an organic or inorganic mold material with at least one nano-element cross-sectional dimension in or close to the nano-scale. These nano-elements can be in various shapes including slits, cones, columns, domes, and hemispheres.

There are two types of nano-elements in this invention: positive nano-elements wherein the nano-element is composed of a mold material (e.g., a polymer) and negative nano-elements wherein the nano-element is a cavity in a mold material (e.g., in a polymer). The nano-pores of this invention are derived from these nano-elements. As seen in FIG. 2A, the nano-element 2 in the positive case is composed of the mold material 1 whereas FIG. 2B shows that the nano-element is a cavity in a mold material.

The present invention affords a tunable pore size and pore spacing based on the mold nano-elements.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying figures in which, relative scale is distorted for visual clarity. In these figures like numerals used with respect to multiple figures correspond to similar materials and structures. While the nano-pore cross-sections in these figures are, for definitiveness, those of a cone or dome-like structure, it is understood that these figures apply to various cross-sectional shapes including those of cones, columns, domes, hemispheres, and slits. Since the figure captions apply to all possible nano-pore shapes, it is noted that within a figure pertaining to this invention cross-sections may appear cone-like or dome-like. Only one pore cross-sectional dimension need be in the nano- or near nano-scale. Actually, for micron scale applications such as cell sorting both cross-sectional dimensions may be in the micron scale.

FIG. 1 A schematic of the prior art capable of producing controlled pore sizes and shapes showing (top view and cross-section AA) a region of a silicon membrane with cone-like pores and (top view and cross-section BB) a region of another silicon membrane with slit-like pores. Currently, systematic nano- and micro-pore arrays with these and other shapes are made in Si with the well-known MEMS/NEMS techniques.

FIG. 2A may also be used directly to make pores by using it to (1) mechanically puncture a membrane material or (2) by using it as a filling mold as seen in Figs C and D. The negative elements of FIG. 2B also may be used in several ways as will be described.

FIG. 2D shows (for the case of 4 being present) material 1 itself is then used as a mold and filled to level 35 with a membrane material or membrane precursor material. The thickness t of this membrane material, the shape of the nano-element, and the nano-element height h determine the nano-pore cross-sectional dimension that will be produced at the actual pore opening at the resulting nano-pore tip. If the coating 4 is present as seen in FIG. 2E, then an etching step or chemo-mechanical polishing (CMP) step to remove layer 4 above 35 will also be needed to create the pore opening at the tip. In either case, the nano-pores are then formed by removing (e.g., dissolution, etching) material 1 giving rise to the nano-porous membrane.

FIGS. 3A-3C are schematics showing nano-element formation by nano-imprinting (FIGS. 3A and B). FIG. 3B depicts negative nano-element formation with the imprinting tool 13 and FIG. 3C depicts positive nano-element formation with a different imprinting tool 13. A optional substrate 10 for support during processing is seen in FIGS. 3 A-C. FIG. 3B can also be used to how the structure of FIG. 2A may be used directly to make pores by using it to mechanically puncture a membrane material 1 in FIG. 3B, in this case membrane material 1 would be chosen to be of composition and thickness to allow full penetration of the cavities 2.

FIG. 4 gives schematics showing nano-element formation by nano-molding. For this approach a master mold 14 is needed as seen in FIG. 4A for creating positive nano-elements as in FIG. 4B. As seen in FIG. 4C a corresponding master mold 14 is used for creating negative nano-elements as in FIG. 4D. Obviously these master molds 14 can be made as shown in FIG. 3. Further, obviously the positive element array made in FIG. 4B can be the master mold used in FIG. 4D.

The master mold 14 of FIG. 4A is then filled to the required depth with the mold material 1 to define and attain the positive nano-elements 2 of FIG. 4B. Correspondingly, the master mold 14 of FIG. 4C is filled to the required depth with the mold material 1 to define and attain the negative nano-elements of FIG. 4D; i.e., to form the cavities 2 which appear on removal of 14.

Figure 5A:
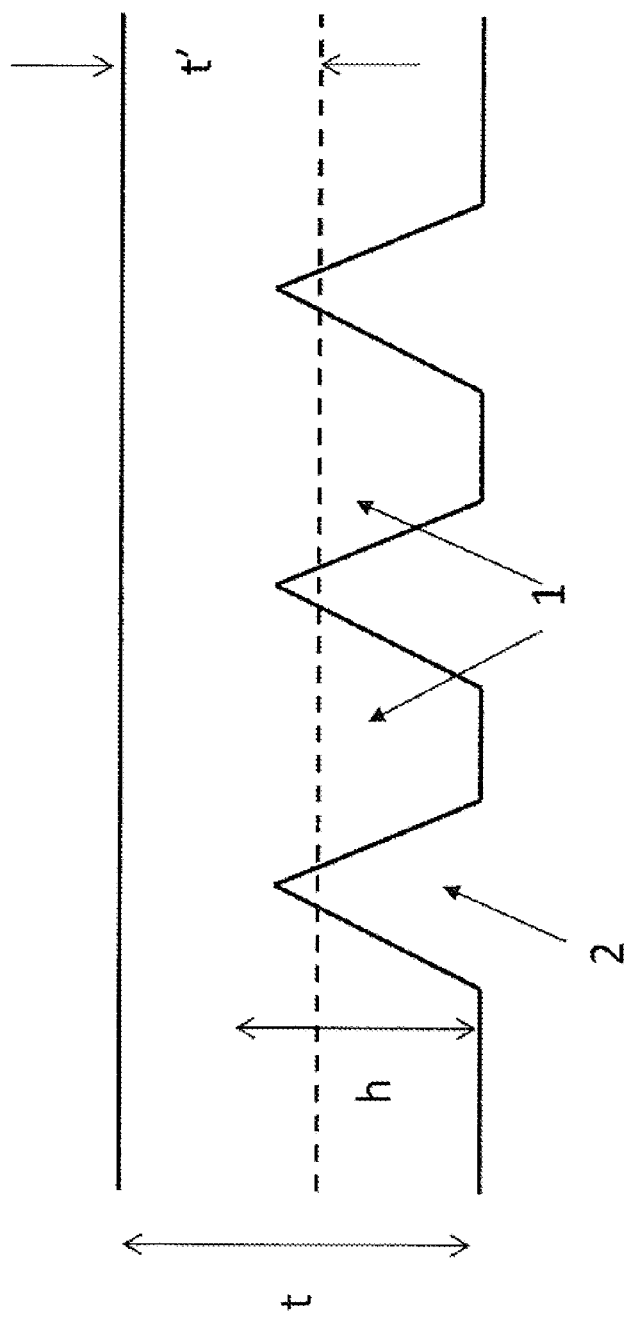
Figure 5B:
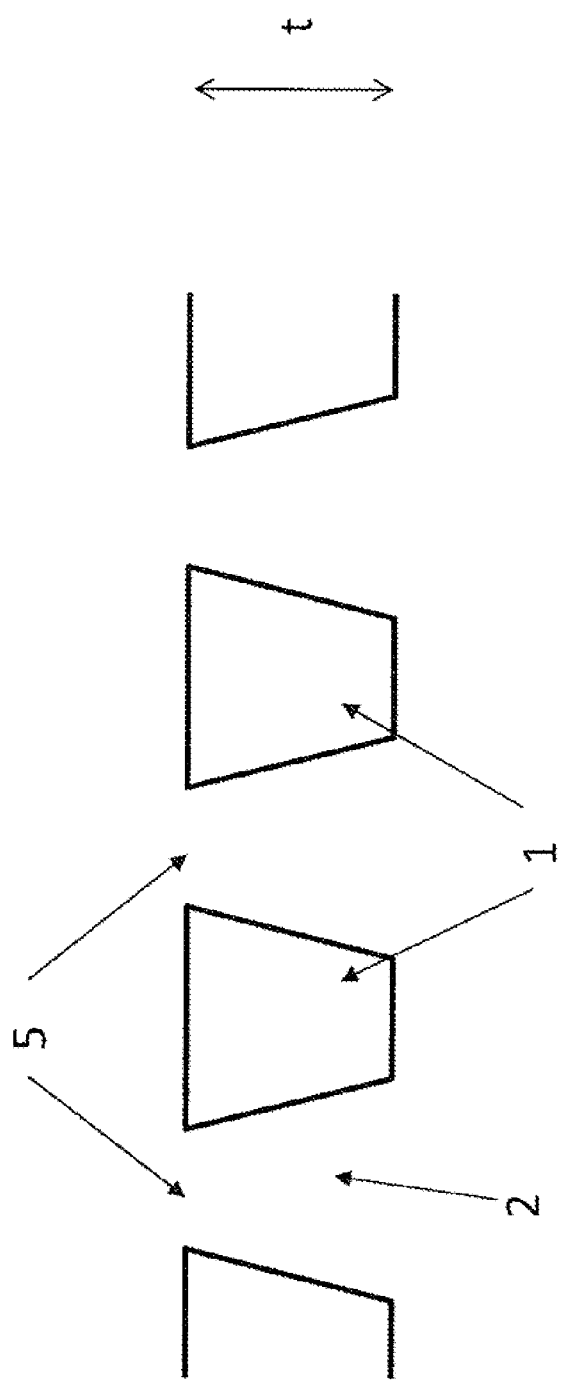
Figure 5C:
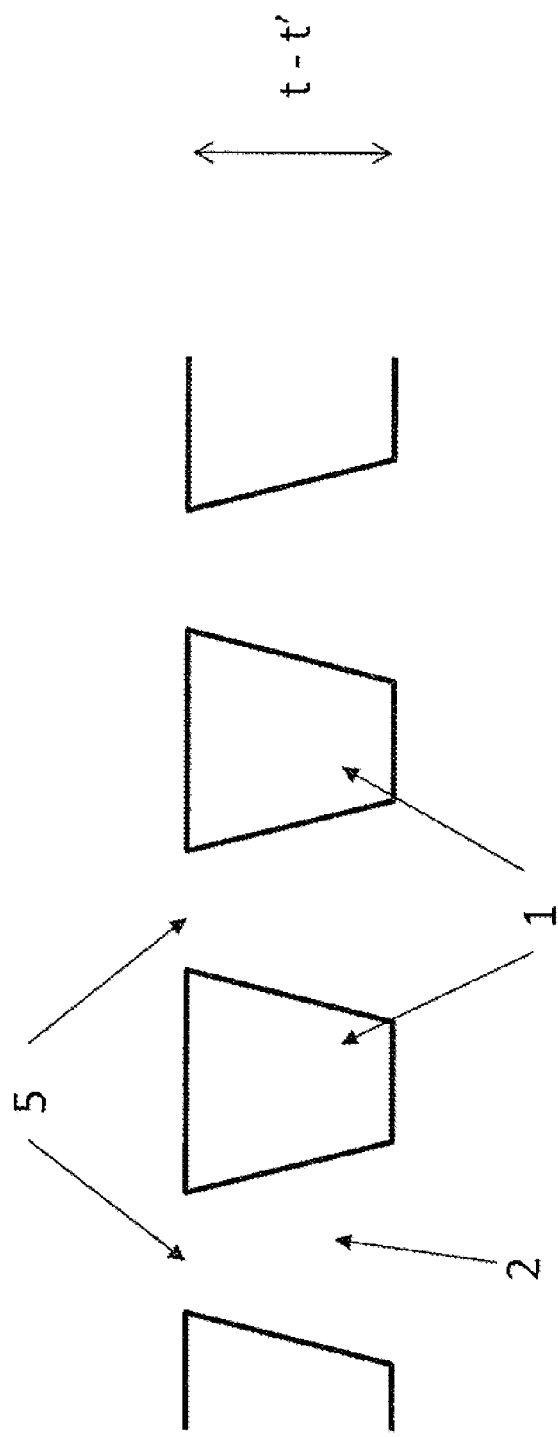
Figure 5D:
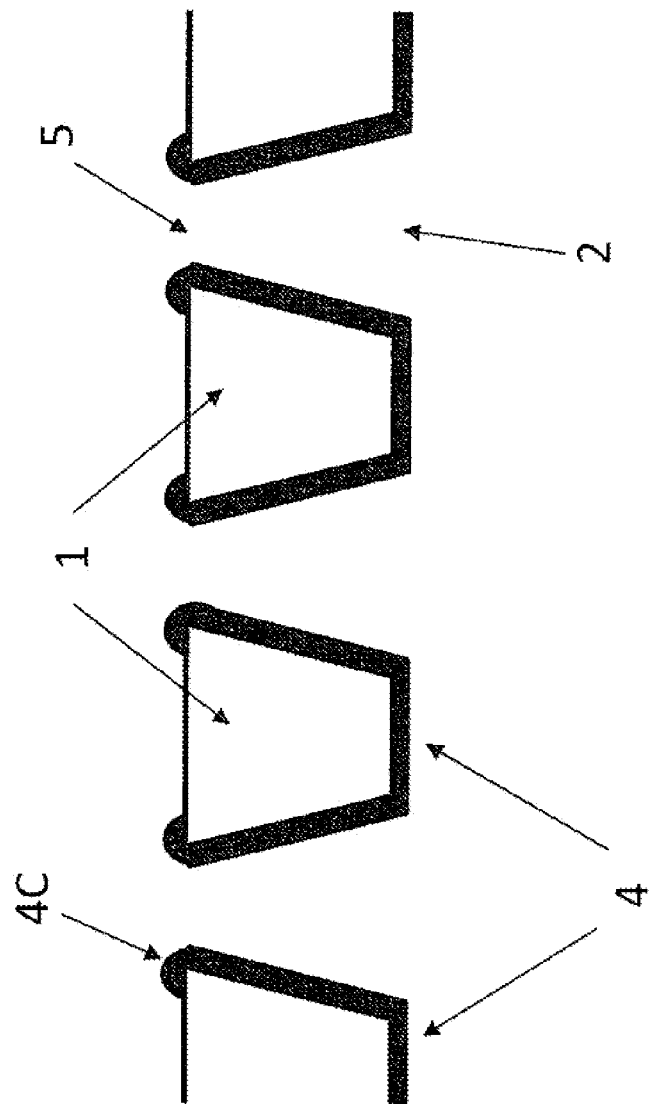
Figure 5E:
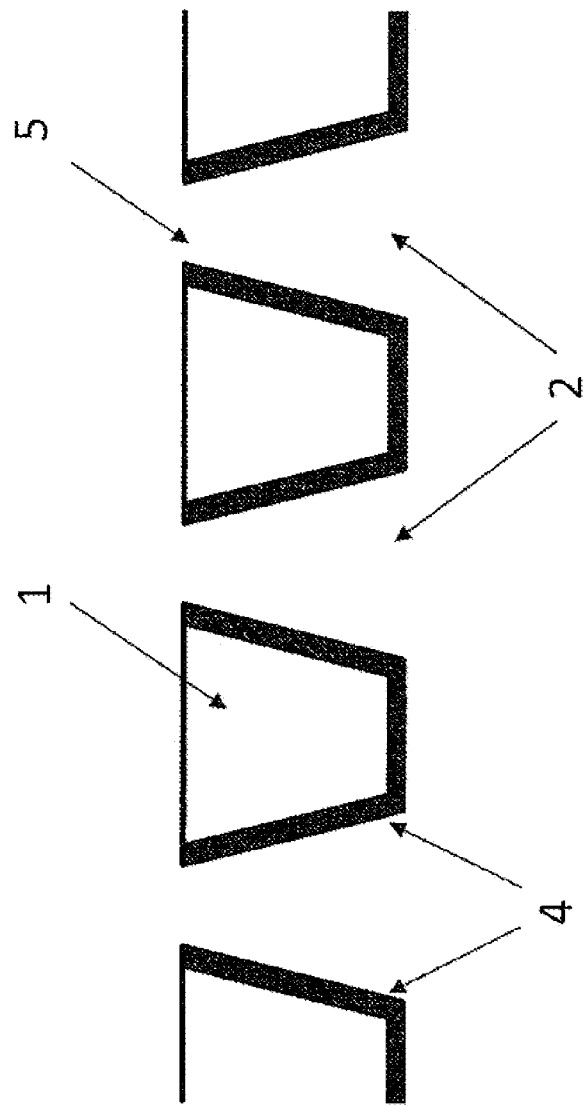

FIGS. 5A-5G. These figures are cross-sectional schematics outlining a number of membrane design possibilities based on negative nano-elements. FIGS. 5D and 5E represent possible completed nano-pore membrane possibilities. The initial schematic (FIG. 5A) depicts nano-elements 2 positioned in mold material 1. These are the empty nano-elements of the negative nano-element approach. If the height h of these nano-elements is greater than t, which is the thickness of the mold material 1, then nano-molding, for example, will actually result in the picture seen in FIG. 5B. This requires 'that the mold material or material precursor fluid, when placed in the master mold, is controlled to achieve h>t. As may be discerned from FIGS. 5A and B, the ratio of h and t will determine the nano-pore size 5. The nano-pore array seen in cross-section in FIG. 5B may also be achieved by removing the volume defined by t' in FIG. 5A. This can be done in controlled manner by dissolution, CMP, or etching (e.g., wet etching, plasma etching). In this case h and t-t' will determine the pore size 5 in FIG. 5C. In either approach, the nano-pore size 5 may be modified by the addition of a coating 4 inside the nano-elements and shown disposed in the examples of FIGS. 5D and E from the back. Highly controlled monolayer-capable techniques such as self-assembly (SAMs) or ALD may be used to further refine the nano-pore size 5 as shown schematically in FIGS. 5F and 5G. In addition transport through nano-pores 5 may be affected by modifying the surface energy at 5. Also as noted earlier, if the coating 4 is a metal or semiconductor, this material may be biased with respect to the medium thereby giving further control of the pore size through modification of the space charge region at the pore with voltage. As is well known, such space charge regions at pores give an effective pore size since they affect ion transport (6-8).

Figure 6:
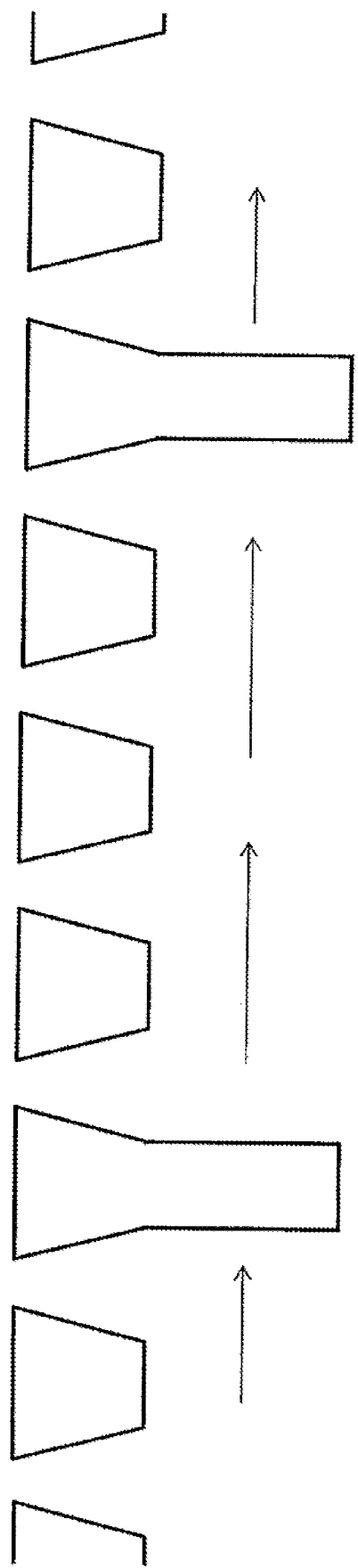

FIG. 6. A schematic showing an exemplary nano-pore filtration membrane with built-in spacers. These spacers can be built-into material 1 during one-step nano-imprinting or nano-molding (FIG. 4). The material defining bottom of flow channel is not shown.

Figure 7:
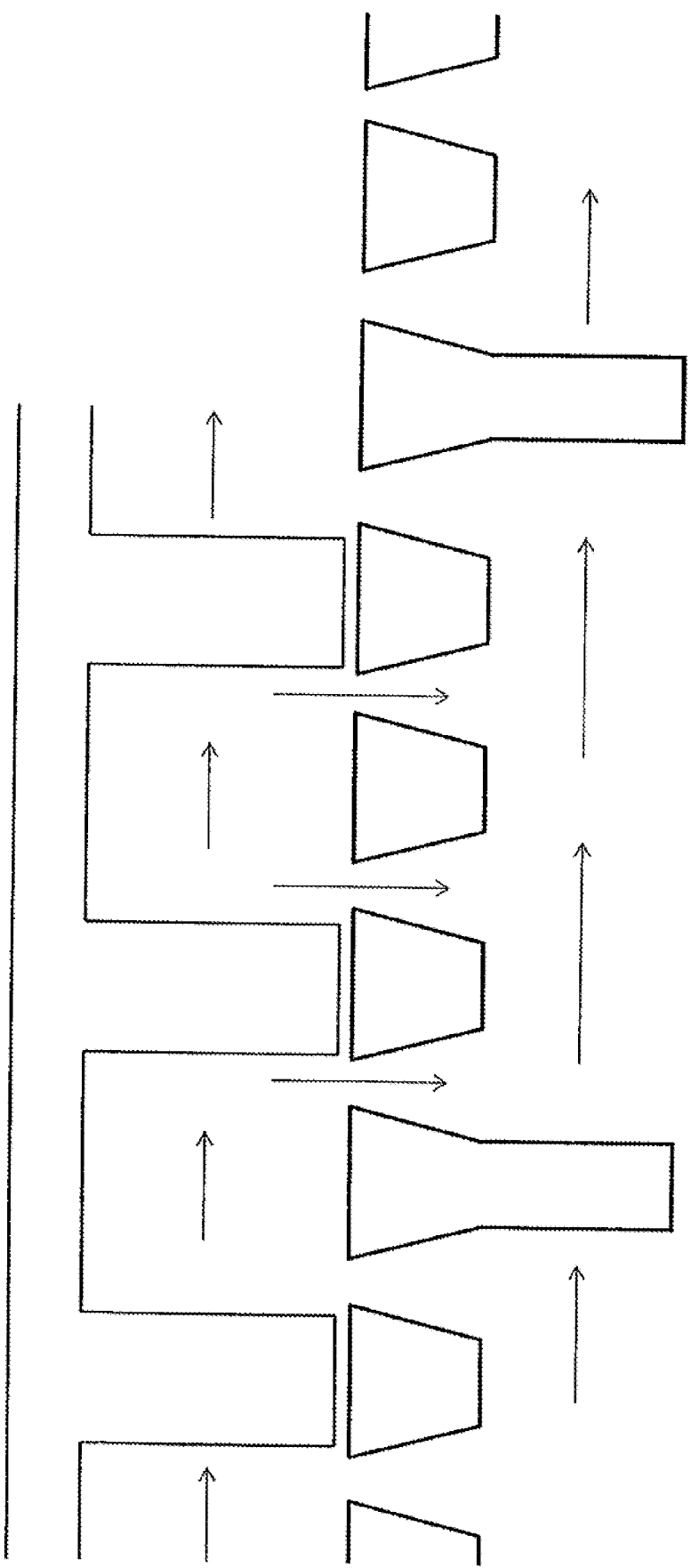

FIG. 7. A schematic showing an exemplary configuration of nano-pore filtration membrane units and flow channel units in series. These units may be stacked and filtration membranes in a stack may have different pore sizes. The material defining bottom of flow channel is not shown.

Figure 8:
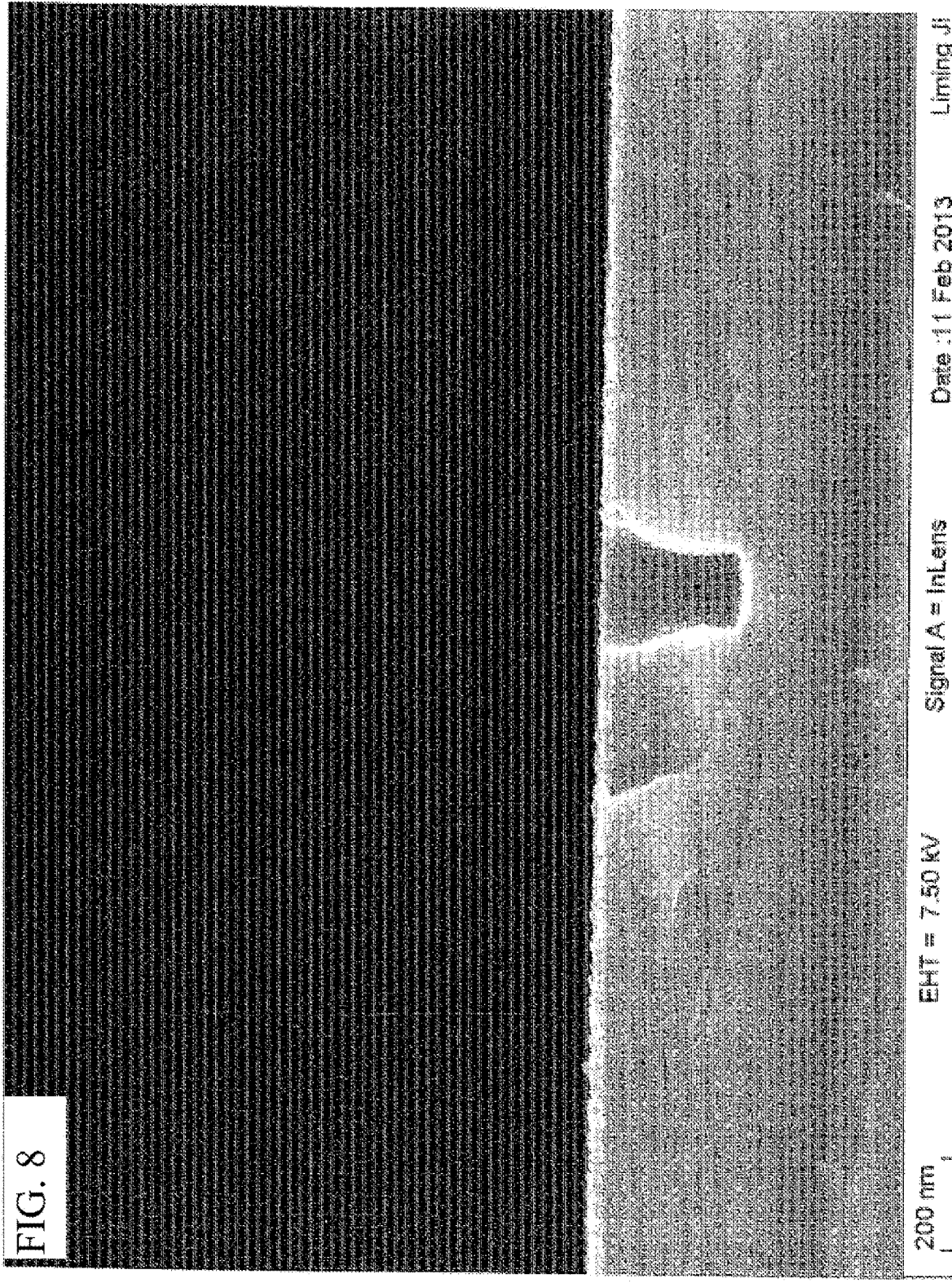

FIG. 8. An FESEM cross-sectional micrograph of a silicon wafer master mold.

Figure 9:
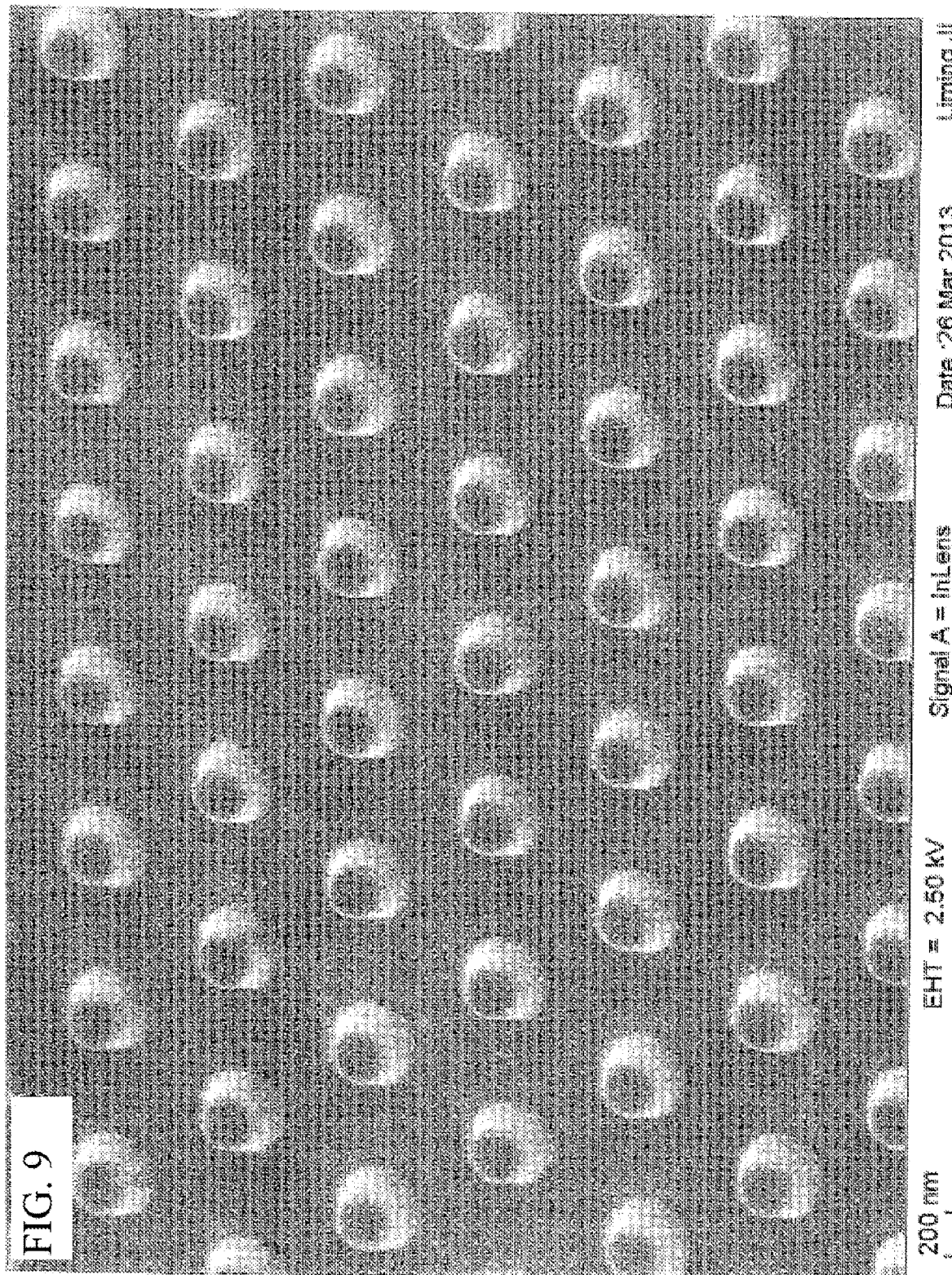

FIG. 9. An FESEM micrograph of a PUA positive nano-element array produced by the master mold of FIG. 8. (30 degree tilted)

Figure 10:
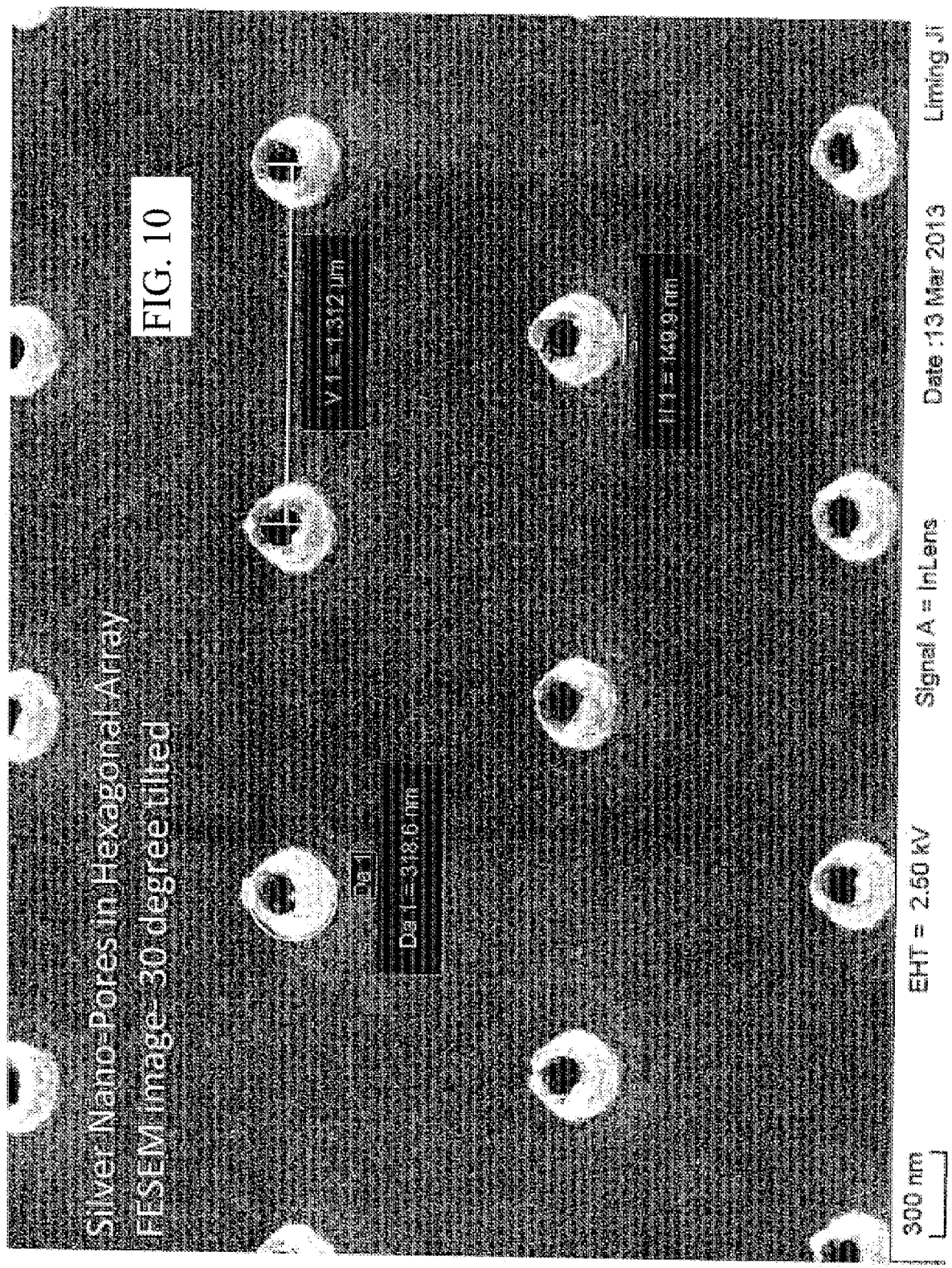

FIG. 10. An FESEM micrograph of Ag nano-pores fabricated by the process steps described in the Example 3.

DETAILED DESCRIPTION OF THE INVENTION

The present invention takes a very different and unique approach to producing pore-bearing membranes. Unlike polymeric membranes or track-etched membranes, it allows for precise pore distributions as well as precise size and shapes without using Si microelectronics-based MEMS/NEMS processing. Further, the manufacturing approach is amenable to continuous roll-2-roll processing opening the door to important cost-savings. The device designs and processing designs presented herein are based on thin film materials and on the utilization of nano-molding and nano-imprinting for pattern transfer. The invention disclosed has the distinct, novel advantages of (1) being able to control pore shape using nano-imprinting or nano-molding processing in a wide variety of inorganic and organic membrane materials, (2) being potentially significantly less expensive to manufacture than MEMS//NEMS approaches since it is based on thin films and nano-imprinting or nano-molding, (3) being manufacturable with roll-to-roll processing due to (3), (4) using a wide variety of organic and inorganic thin film materials as opposed to only using materials amenable to MEMS/NEMS processing, (5) allowing plastic membranes, (6) significantly avoiding Si fouling problems by allowing total avoidance of Si, (7) allowing the tailoring of nano-pore diameters by precise pore size control using techniques such as self-assembling molecules (SAMs) and atomic layer deposition (ALD), (8) allowing the tailoring of nano-pore diameter, selectivity, and transport by pore functionalization using entities such as selected peptides, antibodies, antigens, etc, (9) allowing a version in which electrical biasing of each nano-pore can be achieved thereby allowing precise, and if needed, individual electrical pore size control, (10) allowing a version in which electrical biasing of each nano-pore can be reversed and/or modulated to control pore fouling and (11) having the capability for inherent integration of filtering and flow functions. Current porous membrane designs and processing do not approach these design and processing capabilities and flexibility of materials-use.

This invention uses either positive or negative nano-elements produced by nano-imprinting or nano-molding together with thin film disposition to create micro- or nano-pores and thereby the micro- or nano-pore arrays needed for filtration membranes and drug or chemical injection and monitoring, etc. The invention provides designs and processing flow for producing micro-pores but, more importantly, for producing nano-pores with at least one cross-sectional dimension in or close to the nano-scale. The shapes of these pores can be varied, as desired, from forms such as slits to cones, columns, domes, and hemispheres. The approach of this invention is not limited to using silicon for the membranes nor does it rely on classic MEMS/NEMS processing techniques. It does rely on the use of positive or negative nano-elements with shapes, dimensions, and lattices controlled by nano-imprinting or nano-molding. This freedom from standard MEMS/NEMS pattern transfer and processing techniques allows the use of a wide variety of membrane materials. It also offers the possibility of employing roll-to-roll manufacturing and of significant cost reduction. The latter also is an important point, since, as noted in Ref 4, biomedical devices based on MEMS/NEMS approaches can be relatively costly to manufacture.

The nano-elements basic to this invention can be, as noted, positive or negative nano-elements (FIG. 2). They are positioned in arrays according to some lattice arrangement (e.g., square, hexagonal). Fabrication of these nano-elements and of the arrays in which they are arranged begins with nano-imprinting or nano-molding pattern transfer.

The nano-imprinting/nano-molding methods of pattern transfer employed in this invention both utilize what we have termed a mold material 1. This is seen in FIG. 3 which is schematic showing the nano-imprinting approach for pattern transfer into the mold material 1. The imprinting tool 13 is seen in FIG. 3B to have created, in this example, negative nano-elements 2 in the mold material 1 (e.g., a polymer) of the figure. These nano-elements may go all the way through material 1 directly producing a membrane (materials 1) with pores (cavities 2). There may be a working substrate, as seen in FIG. 3, which is removed after imprinting or may be a mesh-like material giving support but also allowing flow continuity through the pores. As seen in FIGS. 3B and C the mold material must be separated from the imprinting tool 13. This may be done with some combination of mechanical, thermal, or chemical means (i.e., mechanical/chemical means). Imprinting may be used also to give positive nano-elements. This may be noted from FIG. 3C.

FIG. 4 shows schematically how nano-molding can be used for pattern transfer into the mold material 1 for forming the nano-elements. For this approach a master mold 14 is needed as seen in FIG. 4A for positive nano-elements and as seen in FIG. 4C for negative nano-elements. The master mold 14 of FIG. 4A is then filled to the required depth with the mold material 1 to attain the positive nano-elements of FIG. 4B. Correspondingly, the master mold 14 of FIG. 4C is then filled to the required depth with the mold material 1 to attain the negative nano-elements of FIG. 4D. After disposing of the fluid mold material in a master mold, it is solidified (for example, by using photons, heat, etc) yielding the patterned molds 1 of FIG. 4. This figure shows a processing substrate 10 is present. This is not necessary. The molding material in the negative nano-element case or the material applied between positive nano-elements in the positive case is the membrane material and this membrane can serve as its own substrate. As seen in FIGS. 4B and D, the mold material must be separated from the master mold 14. This may be done with some combination of mechanical, thermal, or chemical means (i.e., mechanical/chemical means). This invention provides the advantage of being able to avoid the need for any further separation steps after the separation from 14 in FIG. 4.

Once either nano-imprinting or nano-molding has been chosen to make the nano-elements, various design paths and processing flows are then available depending on whether one has selected positive nano-elements or negative nano-elements. FIGS. 2A, 2C and 2D give cross-sectional schematics outlining membrane designs based on the positive nano-element/thin film concepts of this invention. The positive nano-elements seen in FIG. 2A offer the options of not being coated or of being coated with layer 4 (e.g., a metal, metal/insulator) as shown in FIGS. 2C and D, respectively. When present, material 4 is seen to be disposed on the outside (free) surface and onto the inter-element region of material 1. In either case material 1 is then used as a mold and filled to level 35 with a membrane material or membrane precursor material (possibly requiring thermal annealing, UV exposure, etc). The thickness t of this membrane material, the shape of the nano-element, and the nano-element height h determine the nano-pore cross-sectional dimension that will result at pore 5 of FIG. 2E. If the coating 4 is present, then a processing step (e.g., dry etching, wet etching, CMP) to remove layer 4 above 35 will also be needed. The nano-pores are then formed by removing (e.g., dissolution, etching) material 1 giving rise to the nano-porous membrane seen in FIG. 2E for the case in which layer 4 was not used.

In both positive and negative nano-element approaches highly controlled monolayer-capable disposing techniques such as self-assembly (SAMs) or ALD may be used to further refine the nano-pore size 5. In addition transport through nano-pores 5 may be affected by modifying the surface energy at 5. For example, treatments may be undertaken to render the surface of 5 hydrophobic or hydrophilic. As noted earlier, if layer 4 is present and a metal or semiconductor, this material may be biased with respect to the media on either side of the membrane thereby giving further control of the pore size through modification of the space charge region at the pore with voltage. As is well known, such space charge regions at pores give an effective pore size and can affect ion transport (7-10).

Figure 5F:
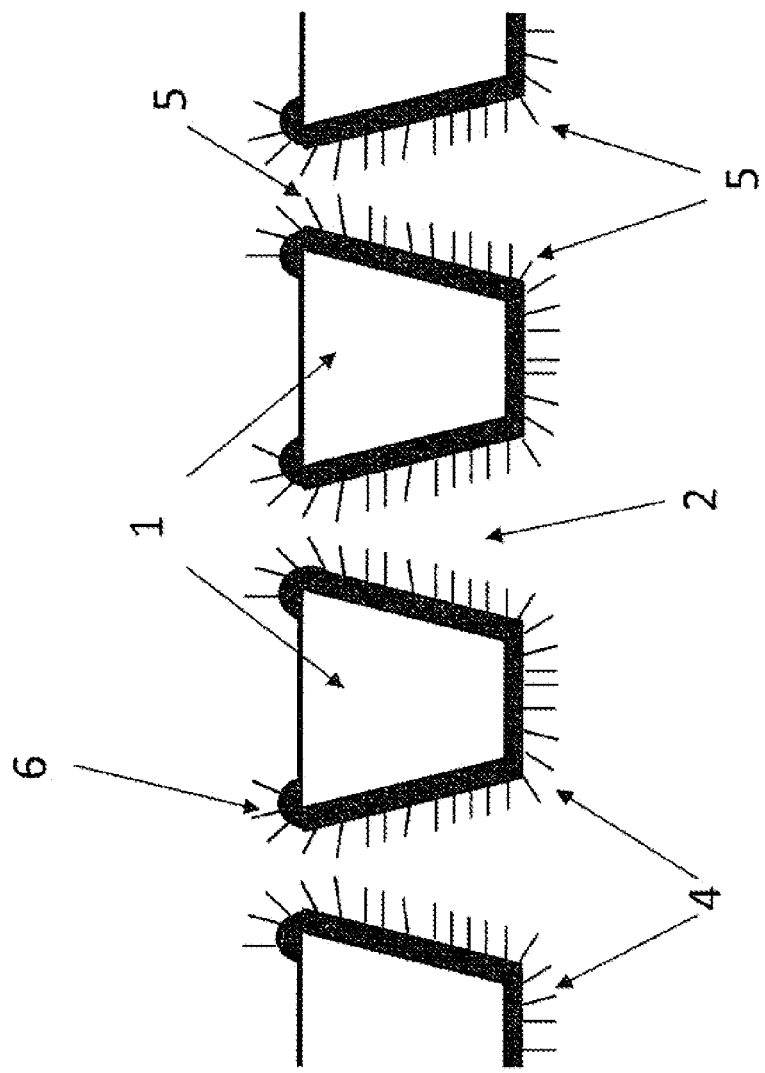
Figure 5G:
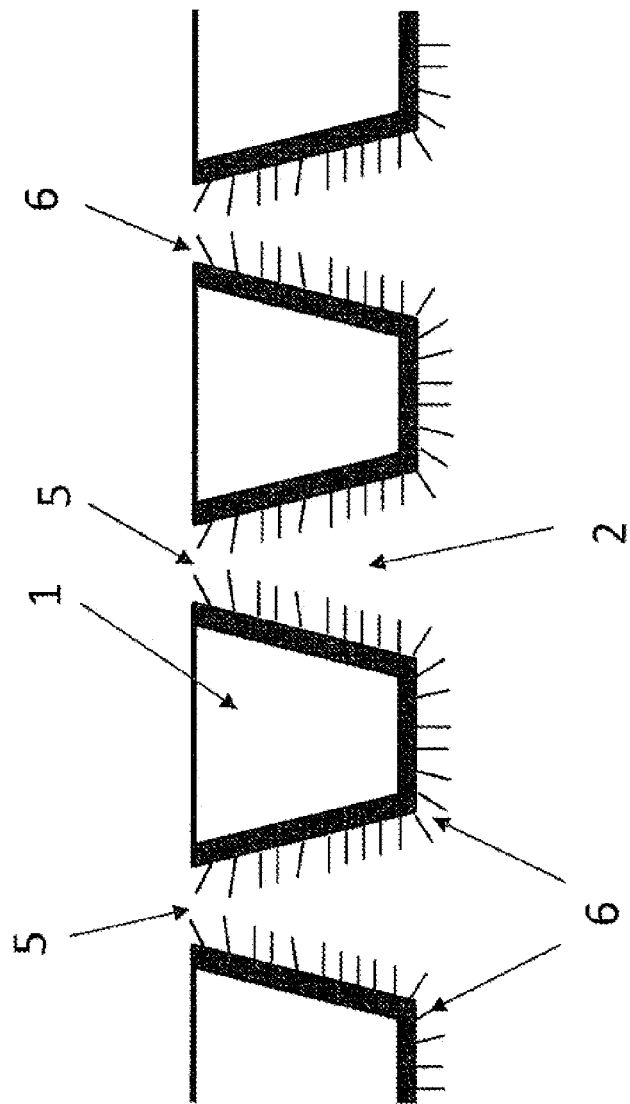

FIG. 5 gives cross-sectional schematics outlining a number of the filtration membrane/drug flow membrane design possibilities based on negative nano-element/thin film concepts of this invention with FIGS. 5F and 5G representing possible completed nano-pore membranes. The initial schematic (FIG. 5A) depicts nano-elements 2 positioned in mold material 1. These are the empty nano-elements of the negative nano-element approach. If the height h of these nano-elements is greater than t, which is the thickness of the mold material 1, then nano-molding, for example, will actually result in the picture seen in FIG. 5B. This requires that the mold material precursor fluid, when placed in the master mold, is controlled to achieve h>t. As may be discerned from FIGS. 5A and B, the nano-element shape as well as the ratio of h and t will determine the nano-pore size 5. The nano-pore array seen in cross-section in FIG. 5B may also be achieved by removing the volume defined by t' in FIG. 5A. This can be done in a controlled manner by dissolution, CMP, or etching (e.g., wet etching, plasma etching). In this case the nano-element shape as well as h and t-t' will determine the pore size 5 in FIG. 5C. In either approach, the nano-pore size 5 may modified by the addition of a coating 4 inside the nano-elements and disposed in the examples of FIGS. 5D and E from the back. We note that the resulting pore shape may be different in FIGS. 5D and E, as shown, since the coating step giving FIG. 5E can be done before removing the volume defined by t'.

Highly controlled monolayer-capable techniques such as self-assembly (SAMs) or ALD may be used to further refine the nano-pore size 5 as shown in FIGS. 5F and 5G. In addition transport through nano-pores 5 may be affected by modifying the surface energy at 5. For example, treatments may be undertaken to render 5 hydrophobic, hydrophilic, etc. As noted earlier, if the coating 4 is a metal or semiconductor, this material may be biased with respect to the media on either side of the membrane thereby giving further control of the pore size and pore allowed flow through modification of the space charge region at the pore with voltage. As is well known, such space charge regions at pores give an effective pore size since they affect ion transport (7-10).

The processing that leads to the nano-pore filtering and drug control membranes depicted in the examples of FIGS. 5B, 5C, 5D, 5E, 5F, and 5G may be used to fabricate flow control units such as that exemplified by FIG. 6A. Here spacers 7 are positioned to allow these flow control units to be located adjacent to or between one or more nano-porous filtration units. FIG. 6B shows an exemplary molding approach to fabricating 6A using mold 14 of FIG. 4. The processing that leads to the nano-pore filtering membranes depicted in the examples of FIGS. 5B, 5C, 5D, 5E, 5F, and 5G may also be used to fabricate nano-pore filtration membranes with built-in spacers such as those seen in FIG. 7. Spacer geometry and positioning is that suitable for the application is chosen. These spacers can be built-into material 1 during nano-imprinting or nano-molding.

Flow control units and filtration membrane units may be arranged in series as seen in FIG. 8. These units may be stacked and filtration membranes in a stack may have different pore sizes. Series and parallel combinations may also be utilized.

The present invention is further detailed with respect the following non-limiting examples. These examples are intended to provide details regarding specific embodiments of the present invention and not to limit the appended claims to the scope of these examples.

Example 1

Example 1 uses a design based on the positive nano-element approach seen in FIG. 2A. The nano-elements 2 could be fabricated by nano-imprinting as shown in FIG. 3C or by nano-molding as shown in FIGS. 4A and 4B. In this example, the latter approach is used. The master mold 14 in this example is single crystal Si. Coated Si (for ware resistance) as well as a variety of other materials, including metals, may be used for the master mold. A silicon wafer, e-beam lithography, and dry etching (e.g., reactive ion etching (RIE)) were used to fabricate the Si master mold 14 (which may be selected to have a variety of shapes including slits, domes, columns, cones, hemispheres) seen in an actual cross-sectional FESEM in FIG. 8 (which is a Si master mold 14 having 'cup-like" shapes). While the master mold is Si, the use of this Si is far different from that in MEMS/NEMS porous membrane design and processing. In this invention the master mold is designed to maintain its integrity and to be reused over and over to create units such as that seen in FIG. 2A. In this example, material 1 of FIGS. 2A and 4B is taken to be polyurethane acrylate (PUA). An actual PUA positive nano-element array is seen in FIG. 9. In approaches such as Example 1 based on positive nano-elements, material 1 must be removable from the master mold, as was achieved here. After formation of the structure seen in FIG. 2A, a membrane material is positioned among the nano-elements to level 35 seen in FIG. 2C using the structure of FIGS. 2A and 2C as a mold.

Any desirable membrane material that is a fluid or whose precursor is a fluid may be utilized. When the thickness of this membrane material t is kept below h, the nano-porous filtration membrane of FIG. 5B results on removal of material 1. This removal can be done by mechanical separation, dry etching, wet etching, and dissolution. The overall nano-pore length L through the membrane is essentially t, which can be up to many microns, if desired.

Example 2

Example 2 also uses a design based on the positive nano-element approach seen in FIG. 2A. The nano-elements 2 are fabricated by nano-molding as shown in FIGS. 4A and 4B. The master mold 14 in this example is again fabricated from single crystal Si. Coated Si as well as a variety of other materials, including metals, may be used for the master mold. A silicon wafer, e-beam lithography, and dry etching (e.g., reactive ion etching (RIE)) were used to fabricate this master mold. In general, if the master mold is Si, the use of this Si is far different from that in MEMS/NEMS, as noted. Here the master mold is designed to maintain its integrity and to be reused over and over to create units such as that seen in FIG. 2A. In this example, material 1 of FIGS. 2A and 4B is taken to be polyimide, a polymer which can withstand processing temperatures up to 450 C. This material is then coated with layer 4 as seen in FIG. 2D. Polymers capable of exposure to elevated temperatures (e.g., polyimide) are required for Example 2 if coating 4 is disposed using elevated temperatures.

Since the coating 4 is positioned on the outside of the nano-elements, void filling by layer 4 inside a nano-element is not utilized. This allows the element height h and therefore overall nano-pore length L through the membrane, to be many microns, if desired.

After formation of the structure seen in FIG. 2D, a membrane material is positioned among the nano-elements to level 35 using the structure of FIG. 2D as a mold. Any desirable membrane material that is a fluid or whose precursor is a fluid may be utilized. When the thickness of this membrane material t is kept below h, the nano-porous filtration membrane of FIG. 5E results after (1) removal of the tip of layer 4 defined by the volume characterized by h-t and (2) subsequent removal of material 1. The tip removal step may be accomplished by, for example, RIE, wet etching, CMP. The resulting overall nano-pore length L through the membrane is essentially t which can be many microns or in the nano-scale, as desired and as controlled by t.

If layer 4 is a metal or semiconductor, the array of nano-pores, with pore region 5, seen in FIG. 5E may be electrically biased with respect to the medium being filtered or monitored. As noted earlier, this allows voltage control of the effective pore size at 5. If layer 4 is a composite composed of an insulator layer on a metal layer, for example, then a dc voltage impressed on the metal (which is interconnected across the bottom of the membrane) will modify current flow at all pores 5 without drawing current. If this metallization across the bottom of the membrane is patterned to define interconnects, array column nano-pore biasing and addressability become possible. If transistors are added at each pore by building on this bottom surface, individual nano-pore biasing and addressability become possible. The filling and/or fouling of nano-pores may be addressed with this Example 2 variant with electric field intervention at the pores 5. If desired, this may be done by varying the biasing to obtain field reversal, field pulsing, or AC field response. These may be done with or without a DC bias and be done continuously, continually, or when flow adjustment is needed.

Example 3

Figure 2B:
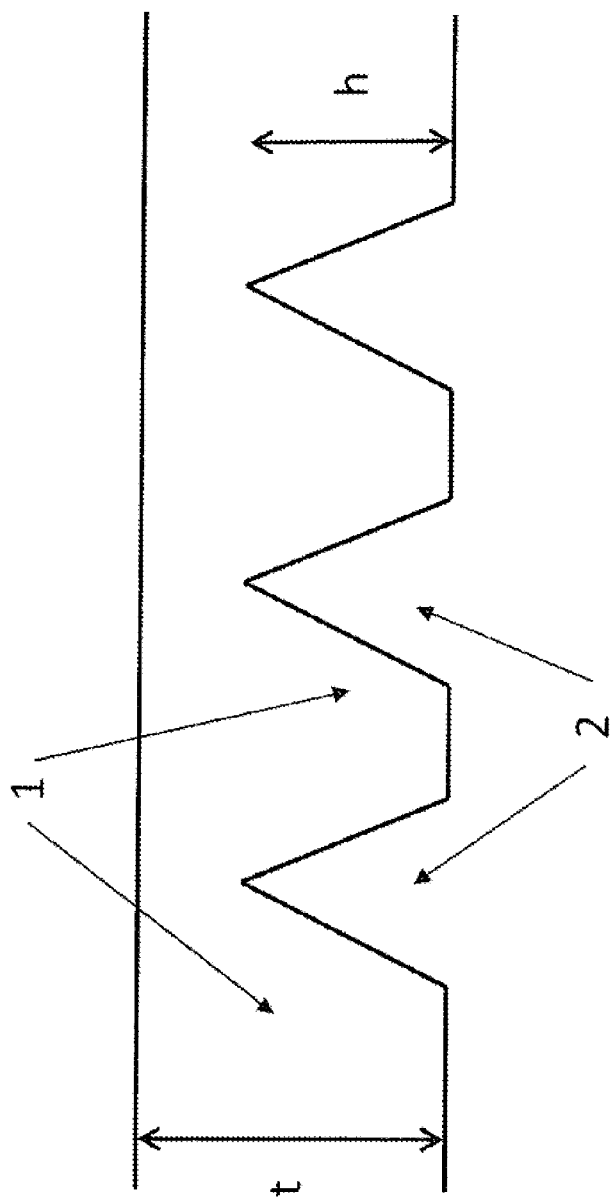
FIGS. 2A and 2B are schematics showing the positive (2A) and negative (2B) nano-element approaches of this invention. The mold material in both cases is denoted by 1 and the nano-element in both cases is denoted by 2. It is important to realize that in this invention methodology, the structure of FIG. 2a may be used as a mold to make the structure of FIG. 2b and vice versa.
Figure 2C:
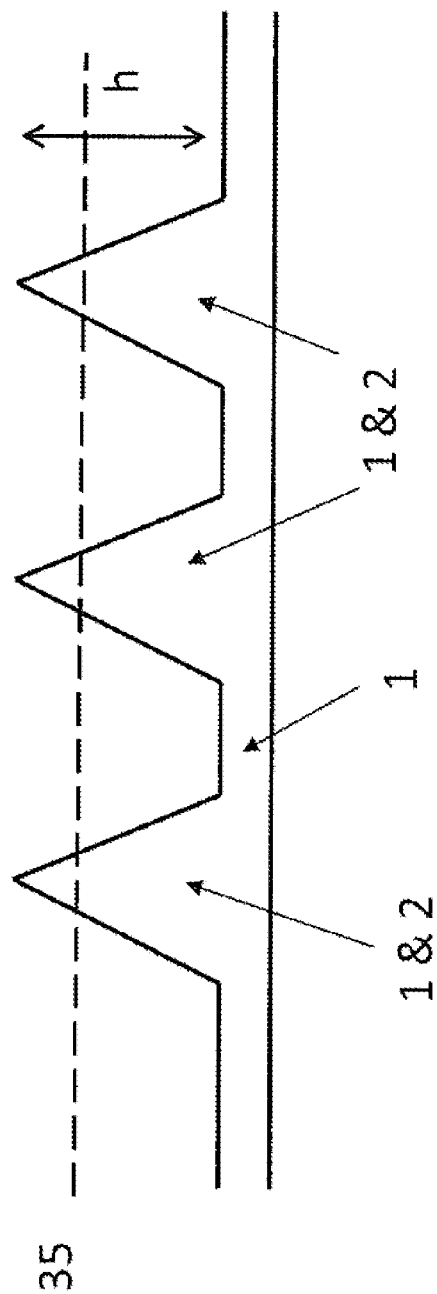
FIGS. 2C and 2D are cross-sectional schematics outlining membrane designs based on filling the positive nano-elements mold. The positive nano-elements seen in FIG. 2A offer the options of not being coated or of being coated with layer 4 (e.g., a metal) shown in FIGS. 2C and D, respectively. Whether layer 4 is or is not present.
Figure 2D:
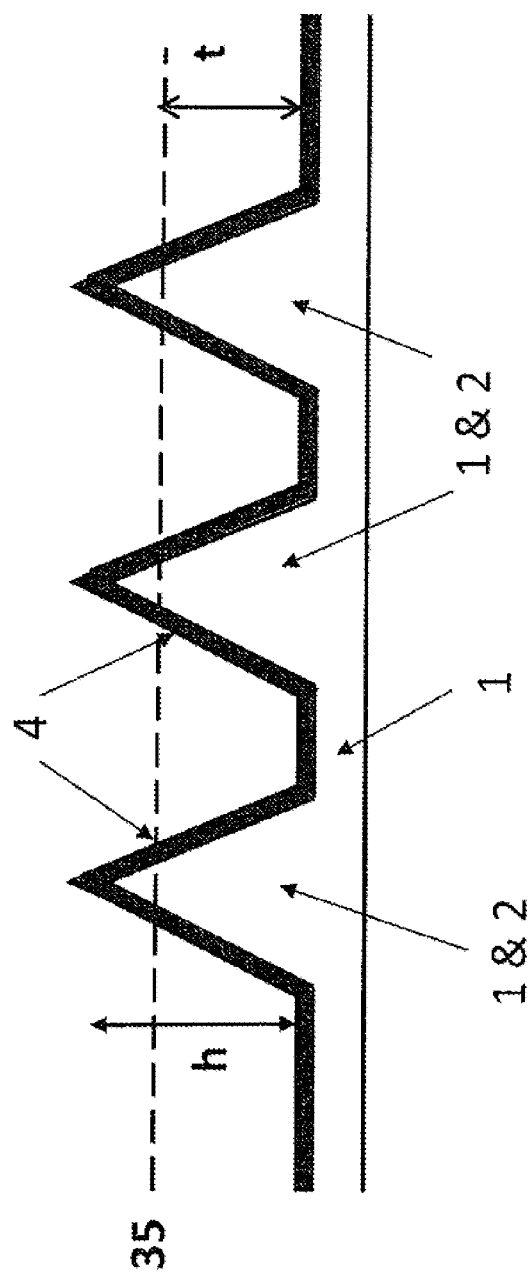
Figure 2E:
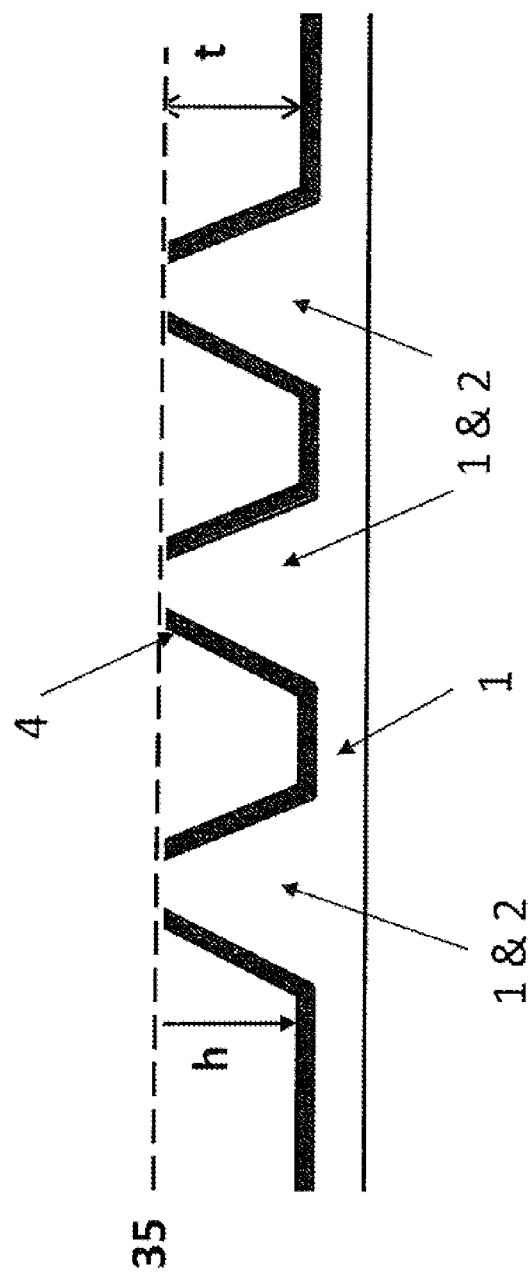

Example 3 uses a design based on the negative nano-element approach seen in FIG. 2B. The empty nano-elements 2 are fabricated by nano-molding as shown in FIGS. 4C and 4D. The master mold 14 in this example is again fabricated from single crystal Si. Coated Si as well as a variety of other materials, including metals, may be used for the master mold. A silicon wafer, e-beam lithography, and dry etching (e.g., reactive ion etching (RIE)) were used to fabricate this master mold. In general, if the master mold is Si, the use of this Si is far different from that in MEMS/NEMS. As is the case in general in this invention, the master mold is designed to maintain its integrity and to be reused over and over to create units such as that seen in FIG. 2B.

In this example 3, the walls of the nano-pores 2 seen in FIG. 2B are subsequently coated with layer 4. The result is the actual array seen in the FESEM micrograph of FIG. 10 for the case in which the layer 4 is sputtered Ag. In the case of this micrograph, after Ag disposition material 1 was mechanically separated to create the nano-pores. As seen in FIG. 10, the resulting membrane has Ag nano-pores supported by an Ag substrate. The region among the nano-pores may be filled with an alternative membrane material if desired and/or the flow unit of FIG. 6 may be added onto the Ag functioning as a membrane. As seen, this mechanical removal resulted in Ag tip removal and pore creation at every nano-pore of FIG. 10. As may be noted from FIG. 10, there are about $10'^2$ m' pores in this membrane. A final membrane material of any thickness t less than the nano-pore height is then disposed using the array of FIG. 10 as the mold. The result as may be inferred from FIG. 10 is a filtration membrane with Ag nano-pores.

REFERENCES

1. S. H. Fissell et al. *High-performance silicon nanopore hemofiltration membranes.* Journal of Membrane Science 326 (2009) 58-63.
2. H. D. Humes et al. *The bioartificial kidney: current status and future promise.* Pediatric Nephrology Journal of the International Pediatric Nephrology Association.© IPNA 201310.1007/500467-013-2467-y
3. W. H. Fissell et al. *Achieving more frequent and longer dialysis for the majority: wearable dialysis and implantable artificial kidney devices.* International Society of Nephrology© 2013.
4. *A better waterworks.* The Economist Technology Quarterly. Jun. 1, 2013.
5. *Allo, allo.* The Economist Technology Quarterly. Jun. 1, 2013.
6. B, Smith, T. Mayer, C. Keating, Deterministic Assembly of Functional nanostructures Using Nonuniform Electric Fields, Annu. Rev. Phys. Chem. 2012. 63:241-63
7. J. Dzubiella and J.-P. Hansen, Electric-field-controlled water and ion permeation of a hydrophobic nanopore, J. Chem. Phys. 122, 234706 (2005)
8. Z. Siwy, I. D. Kosinska, A. Fuliriski, and C. R. Martin, Asymmetric Diffusion through Synthetic Nanopores, Phys. Rev. Lett. 94, 048102 (2005)
9. Matthew R. Powell, Leah Cleary, Matthew Davenport, Kenneth J. Shea, and Zuzanna S. Siwy, Electric-field-induced wetting and dewetting in single hydrophobic nanopores, Nature Nanotechnology 6, 798-802 (2011)
10. A. Nadtochiy, D. Melnikov, and M. Gracheva, Filtering of Nanoparticles with Tunable Semiconductor Membranes, ACS Nano XXX (2013).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A process for the formation of a pore array, the pore array comprising at least one pore having at least one cross-sectional dimension of from 0.2 to 1000 nanometers, the process comprising:

providing an organic or inorganic material substrate with a nano-element array having positive nano-elements, the positive nano-elements being protrusions of the material of a height h;

coating the substrate with a coating layer;

disposing a membrane material of a thickness t less than h on the substrate such that the membrane material is disposed among the positive nano-elements and the thickness t of the membrane material is kept below the height h;

removing the coating layer from the positive nano-elements above the thickness t of the membrane material using etching or chemo-mechanical polishing (CMP);

separating said substrate from the membrane material and the coating layer using dissolution, etching or CMP thereby creating a coated membrane having a pore array with at least one pore in the membrane material, the pore array with the at least one pore having the cross sectional dimension of 0.2 to 1000 nanometers.

2. The process of claim 1, wherein said coating layer controls pore cross-sectional dimensions.

3. The process of claim 1, wherein said coating layer is comprised of at least a SAM material or an ALD material.

4. The process of claim 1, wherein an exposed area of said coating layer is at least partially comprised of a functionalizing layer incorporating at least one of RNA, double stranded DNA, single stranded DNA, peptides, proteins, antibodies, or antigens.

5. The process of claim 1, wherein the composition of said coating layer is a conductor or semiconductor.

6. The process of claim 5, further comprising disposing an insulator layer upon the conductor or semiconductor layer.

7. The process of claim 1, wherein said coating layer controls at least the property of pore dimensionality, pore transport, or specificity.

8. The process of claim 1, further comprising biasing said coating layer with respect to a surrounding media to control one or more of pore effective size, pore flow properties, selectivity, fouling control, and nano-structure positioning.

9. The process of claim 1, wherein the membrane material is a fluid or a precursor of the membrane material is a fluid.

* * * * *